(12) United States Patent
Amemiya et al.

(10) Patent No.: US 6,968,043 B2
(45) Date of Patent: Nov. 22, 2005

(54) X-RAY ANALYZER

(75) Inventors: Masami Amemiya, Tokyo (JP); Masato Ozeki, Tokyo (JP)

(73) Assignees: JEOL Ltd., Tokyo (JP); JEOL Engineering Co., Ltd., Tokyo (JP)

( * ) Notice: Subject to any disclaimer, the term of this patent is extended or adjusted under 35 U.S.C. 154(b) by 129 days.

(21) Appl. No.: 10/626,498

(22) Filed: Jul. 24, 2003

(65) Prior Publication Data

US 2004/0136500 A1    Jul. 15, 2004

(30) Foreign Application Priority Data

Jul. 26, 2002    (JP) .............................. 2002-218126

(51) Int. Cl.[7] .............................................. G21K 3/00
(52) U.S. Cl. ...................................... 378/157; 378/53
(58) Field of Search .................... 378/44–49, 156–158, 378/53, 6; 976/DIG. 435

(56) References Cited

U.S. PATENT DOCUMENTS

| | | | |
|---|---|---|---|
| 4,956,859 A | * | 9/1990 | Lanza et al. ................ 378/157 |
| 5,033,075 A | * | 7/1991 | DeMone et al. ............ 378/156 |
| 5,598,451 A | | 1/1997 | Ohno et al. |
| 6,418,193 B1 | * | 7/2002 | Albagli ....................... 378/158 |
| 2004/0240606 A1 | * | 12/2004 | Laurila et al. ................ 378/45 |
| 2004/0264647 A1 | * | 12/2004 | Graf et al. .................. 378/157 |

FOREIGN PATENT DOCUMENTS

DE    19832973 A1 *    1/2000    .......... G02B 26/00

OTHER PUBLICATIONS

Bertin, Eugene P. "Introduction to X-ray Spectrometric Analysis" Plenum Press, New York 1978, pp. 53,87,93-94.*

* cited by examiner

*Primary Examiner*—Craig E. Church
*Assistant Examiner*—Krystyna Suchecki
(74) *Attorney, Agent, or Firm*—The Webb Law Firm

(57) ABSTRACT

There is disclosed an X-ray analyzer capable of precisely measuring a trace amount of cadmium contained in plastic. The analyzer has an X-ray filter assembly between an X-ray tube having an Rh target and a plastic sample. The filter assembly consists of first, second, and third X-ray filters which are made of zirconium, copper, and molybdenum, respectively. The first through third X-ray filters have thicknesses of about 100 μm, 200 μm, and 40 μm, respectively.

7 Claims, 2 Drawing Sheets

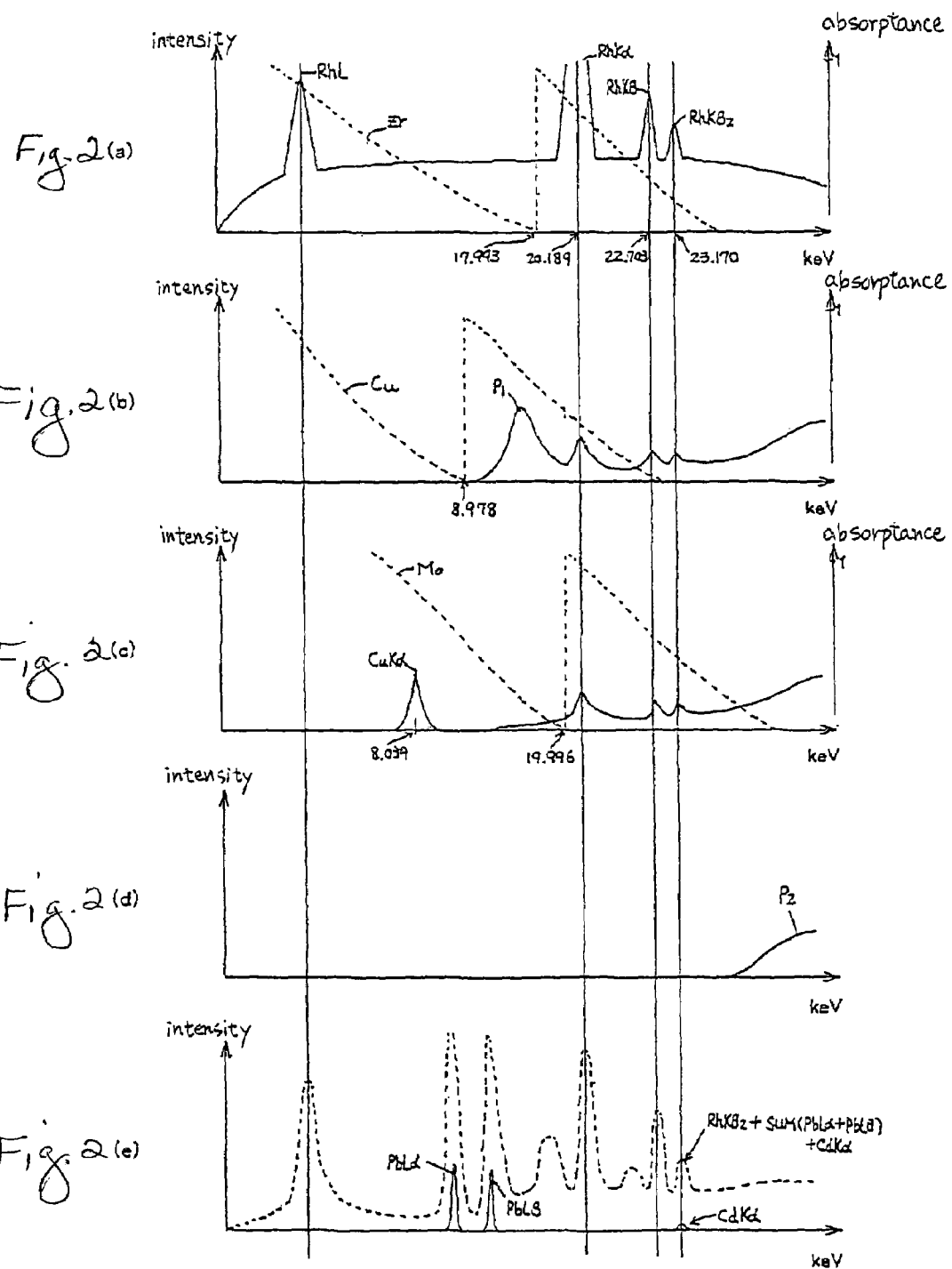

X-RAY ANALYZER

BACKGROUND OF THE INVENTION

1. Field of the Invention

The present invention relates to an X-ray analyzer, such as an X-ray fluorescent analyzer.

2. Description of Related Art

In recent years, the Earth's environmental problems have deteriorated increasingly and become more complicated. In response to these global environmental problems, the European Union (EU) has issued a Directive on Waste Electrical and Electronic Equipment (WEEE) and a Directive on the restriction of the use of certain hazardous substances (ROHS). The EU has sounded an alarm by legislating the hazardness. The substances which have been limited in use by the ROHS are 6 substances, i.e., cadmium (Cd), lead (Pb), mercury, hexavalent chromium, poly-brominated biphenyl (PBB), and poly-brominated diphenylether (PBDE).

Components used in electric and electronic devices distributed today are mostly made of plastics. These plastics contain cadmium and lead that are banned from use by the ROHS directive. Accordingly, in recent years, it has become necessary to precisely measure the amounts of cadmium and lead contained in plastics.

With the existing analytical apparatus, however, trace amounts of cadmium from several ppm to tens of ppm contained in plastics cannot be analyzed precisely. Furthermore, if an X-ray fluorescent analyzer that is one kind of analytical apparatus is used, accurate analysis results have not been obtained because of the backgrounds of the X-ray spectra derived by X-ray fluorescent analysis. In particular, the background level of such a spectrum of a trace amount of cadmium is considerably high compared with spectral peaks. That is, the peak/background ratio (P/B) is considerably low.

SUMMARY OF THE INVENTION

In view of the foregoing, the present invention has been made.

It is an object of the present invention to provide an X-ray analyzer capable of precisely quantitating a trace amount of cadmium contained in plastic.

This object is accomplished in accordance with the teachings of the invention by an X-ray analyzer having an X-ray tube emitting primary X-rays toward a sample to thereby excite secondary X-rays from the sample. The secondary X-rays are detected to analyze the sample. This X-ray analyzer has a first X-ray filter for filtering out primary X-rays from the target in the X-ray tube, a second X-ray filter for filtering out X-rays emerging from the first X-ray filter, and a third X-ray filter for filtering out X-rays emerging from the second X-ray filter. These three filters are mounted between the target in the X-ray tube and the sample.

Other objects and features of the invention will appear in the course of the description thereof, which follows.

BRIEF DESCRIPTION OF THE DRAWINGS

FIGS. 2(a)–2(e) are graphs illustrating the operation of the apparatus shown in FIG. 1.

DESCRIPTION OF THE PREFERRED EMBODIMENTS

Figure 1:
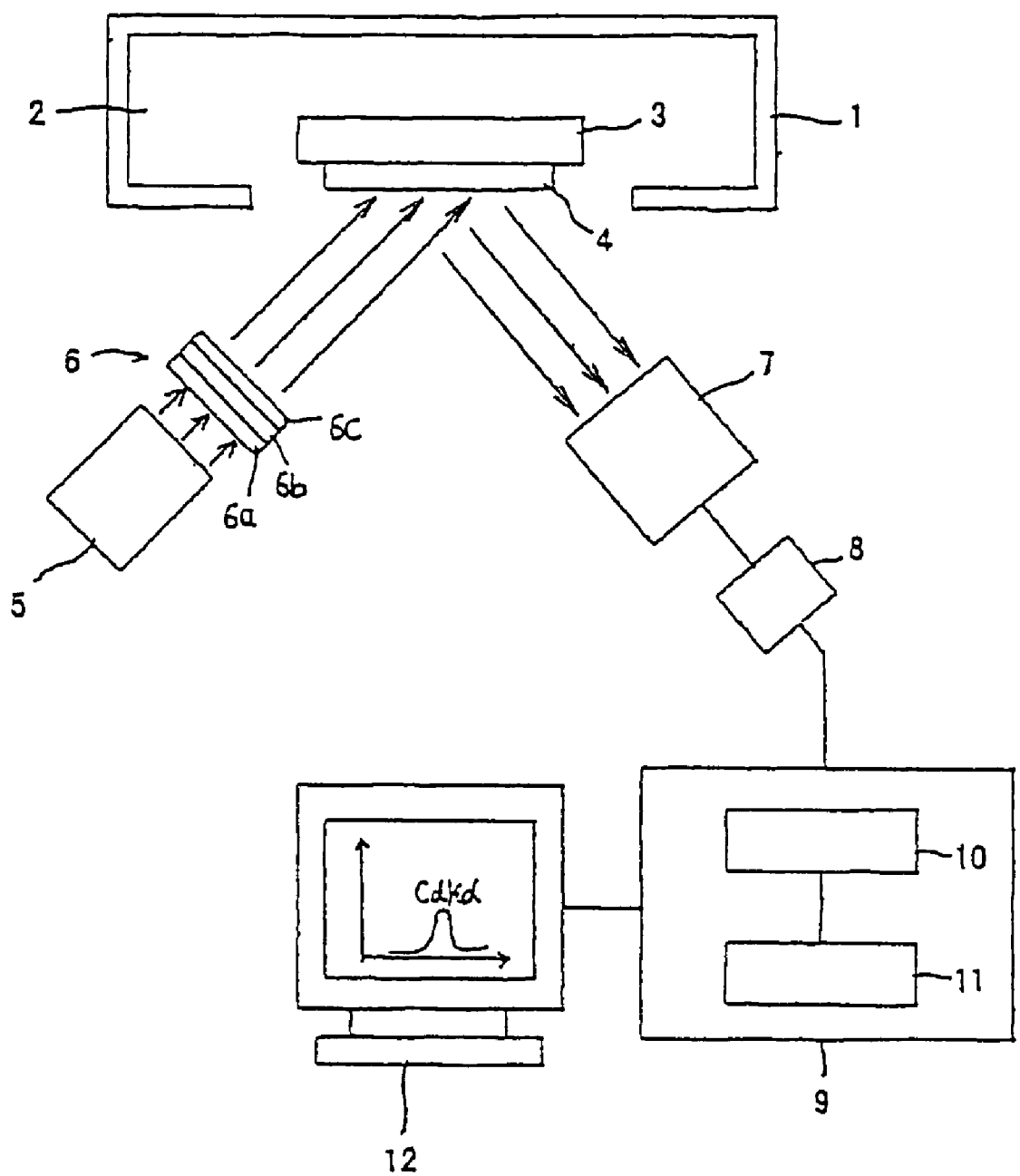
FIG. 1 is a block diagram of an X-ray analyzer according to the present invention.

FIG. 1 shows an X-ray analyzer according to the present invention. This apparatus is an X-ray fluorescent analyzer fitted with an energy-dispersive X-ray spectrometer (EDS).

Referring still to FIG. 1, the analyzer has a sample chamber cover 1 and a sample chamber 2. A sample holder 3 is placed within this sample chamber 2. A sample of a plastic 4 is set in the sample holder 3. The plastic 4 contains about 1% of lead and several ppm to tens of ppm of cadmium.

An X-ray tube 5 has a target made of rhodium (Rh). An X-ray filter assembly 6 is positioned between the X-ray tube 5 and the sample 4. This X-ray filter assembly 6 has a first X-ray filter 6a consisting of a circular foil of zirconium, a second X-ray filter 6b consisting of a circular foil of copper, and a third X-ray filter 6c consisting of a circular foil of molybdenum. These first, second, and third filters 6a–6c are placed in this order from the X-ray tube 5 toward the sample 4 as shown in FIG. 1. These filters 6a–6c are about 100 $\mu$m, 200 $\mu$m, and 40 $\mu$m, respectively, thick.

Referring still to FIG. 1, X-rays from the sample 4 are detected by a semiconductor X-ray detector 7. The output signal from this detector 7 is applied to a microchannel analyzer (MCA) 8. The output signal from the MCA 8 is applied to a central processing unit (CPU) 9.

The microchannel analyzer (MCA) 8 separates, or sorts, the output signal from the semiconductor X-ray detector 7 according to energy. An X-ray intensity signal corresponding to each energy is accumulated and stored in a storage portion 10 of the CPU 9. That is, as analysis of the sample progresses, the intensity of the X-ray intensity signal increases. Data stored in the storage portion 10 is sent to a spectral display portion 11 of the CPU 9. The spectral display portion 11 displays an X-ray spectrum on the viewing screen of a display device 12 according to the data. For example, the spectral display portion 11 is currently so set that an X-ray spectrum regarding CdK$\alpha$ peak is displayed on the viewing screen of the display device 12.

The structure of the apparatus of FIG. 1 has been described so far. The operation is described below. When the plastic sample 4 is being analyzed, a given voltage of V1 is applied between an X-ray tube filament (not shown) and the Rh target. The electron beam from the X-ray tube filament hits the Rh target. As a result, primary X-rays are radiated from the Rh target. The solid line in FIG. 2(a) shows an X-ray spectrum created by the primary X-rays emitted from the Rh target.

As can be seen from the X-ray spectrum of FIG. 2(a), the X-ray spectrum created by the primary X-rays emitted from the Rh target of the X-ray tube 5 contains RhL peak, RhK$\alpha$ peak, RhK $\beta$ peak, and RhK $\beta_2$ peak which are present against a high level of background. The energy (wavelength) of CdK$\alpha$ line of cadmium is 23.127 keV, which is approximately equal to the energy (23.170 keV) of RhK$\beta_2$ line.

The primary X-rays emitted from the Rh target of the X-ray tube 5 first enter the first filter 6a of the X-ray filter assembly 6. This first filter 6a is made of a foil of zirconium. The broken line of FIG. 2(a) indicates the absorption characteristics of the zirconium (Zr). The energy of the absorption edge of Zr is 17.993 keV, which is slightly lower than the energy (20.189 keV) of RhK$\alpha$ line.

In the first filter 6a made of Zr in this way, the primary X-rays from the X-ray tube 5 are partially absorbed. The solid line of FIG. 2(b) indicates an X-ray spectrum of the primary X-rays which have emerged from the first filter 6a and are yet to enter the second filter 6b.

As can be seen from the X-ray spectrum of FIG. 2(b), the X-ray spectrum created by the primary X-rays passed through the first filter 6a has peaks $P_1$, RhKα, RhKβ, and RhKβ$_2$ having energies close to the absorption edge of Zr. However, the intensities of these peaks RhKα, RhKβ, and RhKβ$_2$ are much weakened compared with the case of FIG. 2(a). Also, the background against which these peaks are present is much lower than in the case of FIG. 2(a).

The primary X-rays emerging from the first filter 6a enter the second filter 6b, which consists of a foil of copper. The broken line of FIG. 2(b) indicates the X-ray absorption characteristics of the copper (Cu). As shown in this FIG. 2(b), the energy of the absorption edge of Cu is 8.978 keV.

In the second filter 6b consisting of Cu in this way, the primary X-rays passed through the first filter 6a are partially absorbed. The solid line of FIG. 2(c) shows an X-ray spectrum created by the primary X-rays which have emerged from the second filter 6b and are yet to enter the third filter 6c.

As can be seen from the X-ray spectrum of FIG. 2(c), the X-ray spectrum created by the primary X-rays emerging from the second filter 6b still contains peaks Rhα, RhKβ, and RhKβ$_2$ in the same way as in the case of FIG. 2(b). However, the peak $P_1$ of FIG. 2(b) does not exist in the X-ray spectrum of FIG. 2(c). On the other hand, the X-ray spectrum of FIG. 2(c) has a new CuKα peak. This is produced because the second filter 6b of copper foil is excited by the primary X-rays.

Then, the primary X-rays passed through the second filter 6b enter the third filter 6c, which consists of molybdenum foil. The broken line of FIG. 2(c) indicates the X-ray absorption characteristics of the molybdenum (Mo). As shown in FIG. 2(c), the energy of the absorption edge of Mo is 19.996 keV.

The primary X-rays passed through the second filter 6c are partially absorbed by the third filter 6c made of Mo as described above. FIG. 2(d) shows an X-ray spectrum created by the primary X-rays passed through the third filter 6c.

As can be seen from the X-ray spectrum of FIG. 2(d), the X-ray peaks present in FIGS. 2,(a)–(c), are not present in the X-ray spectrum created by the primary X-rays passed through the third filter 6c. Furthermore, the primary X-rays producing a background are suppressed over a wide range. In FIG. 2(d), only X-ray intensities are shown in a part $P_2$ that is higher than the energy position of RhKβ$_2$ line. This is due to primary X-rays (XH) having energies still higher than that of RhKβ$_2$ line.

Accordingly, if such primary X-rays (XH) strike the plastic sample 4, primary X-rays reflected by the sample 4 and detected by the detector 7 are only the primary X-rays (XH). Primary X-rays having lower energies are not detected. This means that no background is produced. On the other hand, the primary X-rays (XH) have a sufficient level of energy to excite cadmium (Cd) and lead (Pb) in the plastic.

As a result, an X-ray intensity signal as indicated by the solid line in FIG. 2(e) is finally stored in the storage portion 10 of the CPU 9. The CdKα peak appearing here is produced only by the CdKα line generated from the plastic sample 4. Background due to other X-rays is not contained in it. Similarly, the PbLα peak and PbLβ peak appearing here are created only by the PbLα and PbLβ lines, respectively, which are produced from the plastic sample 4. Background due to other X-rays is not contained in it. The broken line in FIG. 2(e) indicates an X-ray spectrum obtained when no filter is placed between the X-ray tube and sample.

Therefore, the CPU 9 can obtain precise quantitative analysis results by finding the trace amounts of cadmium and lead in the plastic sample 4 based on the data stored in the storage portion 10. The spectral display portion 11 displays an X-ray spectrum about the CdKα peak on the viewing screen of the display device 12.

In the past, in X-ray fluorescent analysis of plastic containing lead (Pb), a sum peak of Pb has pushed up the background level of the CdKα spectral peaks on an X-ray spectrum. This rise in the background level is most conspicuous where PbLα and PbLβ lines of x-rays are detected at the same time. In the present invention, the appearance of such sum peaks can be suppressed for the following reason. Only primary X-rays (XH) having a sufficient level of energy to excite cadmium (Cd) and lead (Pb) are made to strike the sample as mentioned previously. Thus, the amount of primary X-rays hitting the sample is limited compared with the prior art. Consequently, the probability of occurrence of sum peaks of Pb can be reduced immensely.

While the X-ray fluorescent analyzer of FIG. 1 has been described, it is to be understood that the present invention is not limited to this embodiment. For example, in the embodiment described above, the second X-ray filter may be made of zinc or nickel.

Furthermore, the first X-ray filter may be made of copper, zinc, or nickel. The second X-ray filter may be made of zirconium. The third X-ray filter may be made of molybdenum. In addition, the first X-ray filter may be made of copper, zinc, or nickel. The second X-ray filter may be made of molybdenum. The third X-ray filter may be made of zirconium.

Where the target of the X-ray tube is made of molybdenum, if the first X-ray filter is made of molybdenum, the second X-ray filter is made of copper, zinc, or nickel, and the third X-ray filter is made of molybdenum, then the same advantages as produced by the above-described embodiment can be obtained. At this time, the thicknesses of the first, second, and third X-ray filters should be set to approximately 80 μm, 200 μm, and 40 μm, respectively.

Having thus described our invention with the detail and particularity required by the Patent Laws, what is desired to be protected by Letters Patent is set forth in the following claims.

The invention claimed is:

1. An X-ray analyzer for making an analysis of a sample by directing primary X-rays from a target in an X-ray tube at the sample to excite secondary X-rays from the sample and detecting the excited secondary X-rays, said X-ray analyzer comprising:
   a first X-ray filter for filtering out primary X-rays from the target in the X-ray tube;
   a second X-ray filter for filtering out X-rays emerging from the first X-ray filter; and
   a third X-ray filter for filtering out X-rays emerging from the second X-ray filter; and
   an X-ray detector for detecting secondary X-rays from the sample,
   wherein said first through third X-ray filters are located between the target in the X-ray tube and the sample.

2. The X-ray analyzer of claim 1, wherein said third X-ray filter absorbs X-rays which are excited by said primary X-rays and produced from one of said first and second X-ray filters.

3. The X-ray analyzer of claim 1, wherein said second X-ray filter absorbs X-rays which are excited by said primary X-rays and produced from said first X-ray filter.

4. An X-ray analyzer of claim 1 or 2, wherein the target in the X-ray tube consists of rhodium,
- wherein said first X-ray filter consists of zirconium,
- wherein said second X-ray filter consists of one of copper, zinc, and nickel, and
- wherein said third X-ray filter consists of molybdenum.

5. An X-ray analyzer of claim 1 or 2,
- wherein the target in the X-ray tube consists of rhodium,
- wherein said first X-ray filter consists of one of copper, zinc, and nickel,
- wherein said second X-ray filter consists of zirconium, and
- wherein said third X-ray filter consists of molybdenum.

6. An X-ray analyzer of claim 1 or 3,
- wherein the target in the X-ray tube consists of rhodium,
- wherein said first X-ray filter consists of one of copper, zinc, and nickel,
- wherein said second X-ray filter consists of molybdenum, and
- wherein said third X-ray filter consists of zirconium.

7. An X-ray analyzer of claim 1 or 2,
- wherein the target in the X-ray tube consists of molybdenum,
- wherein said first X-ray filter consists of molybdenum,
- wherein said second X-ray filter consists of one of copper, zinc, and nickel, and
- wherein said third X-ray filter consists of molybdenum.

* * * * *